United States Patent [19]

Sugiyama et al.

[11] Patent Number: 4,573,465

[45] Date of Patent: Mar. 4, 1986

[54] LASER IRRADIATION APPARATUS

[75] Inventors: Seiji Sugiyama, Kanagawa; Norihiro Suenaga; Nobuyuki Suenaga; Michihiro Kaneda, both of Kanagawa, all of Japan

[73] Assignee: Nippon Infrared Industries Co., Ltd., Tokyo, Japan

[21] Appl. No.: 442,082

[22] Filed: Nov. 16, 1982

[30] Foreign Application Priority Data

Nov. 19, 1981 [JP] Japan .............................. 56-186165

[51] Int. Cl.⁴ .............................................. A61B 17/36
[52] U.S. Cl. .................................. 128/303.1; 128/395; 219/121 LS; 372/23
[58] Field of Search ...................... 128/303.1, 395–398; 219/121 LS; 372/23, 25

[56] References Cited

U.S. PATENT DOCUMENTS 4,338,578  7/1982  Sukhman ............................... 372/23
4,408,602  10/1983 Nakajima ......................... 128/303.1

FOREIGN PATENT DOCUMENTS 2809007  9/1979  Fed. Rep. of Germany ...... 128/395

Primary Examiner—Lee S. Cohen
Attorney, Agent, or Firm—Cushman, Darby & Cushman

[57] ABSTRACT

A laser irradiating apparatus which irradiates a plurality of working laser beams having different wave-lengths to obtain complex effects in medical treatments. The outputs of the laser beams are controlled, and the output ratio of the laser beam is selectively set for various irradiating conditions so that the medical treatments for various living organisms can be carried out under the most desirable irradiating condition.

3 Claims, 4 Drawing Figures

LASER IRRADIATION APPARATUS

BACKGROUND OF THE INVENTION

1. Field of the Invention

This invention relates to a laser irradiation apparatus, more particularly to a laser irradiation apparatus which irradiates a plurality of laser beams.

2. Description of the Prior Art

It is known that the interaction between a substance and a ray varies according to the wave-length of the ray and the property constants of materials irradiated with the ray. The constants include a reflectivity, absorption coefficient, scattering coefficient, thermal conductivity, and thermal diffusion constant. Particularly, the reflectivity, absorption coefficient and scattering coefficient have dependence on the wave-length.

For example, it is known that the absorption coefficient depends on various absorption factors in the material and in the case of solid materials, there can be mentioned basic absorption by interband transition, free electron absorption, grid absorption (phonon absorption), impurity absorption, and so on. These absorptions depend on the wave-length of ray inputs.

Also, in the case of a living organism, similar phenomenons occur. Water which is a predominant component of the living organism has an absorption band according to the vibration of water molecules in the infrared range. In the visible range, there exists absorption due to the presence of hemoglobin. Further, the scattering coefficient in a living organism is the factor which must be taken into consideration.

Thus, when a laser of a specific wave-length is irradiated on an object, the effect of the irradiation varies largely depending on the oscillation wave-length. For example, if a $CO_2$ laser beam which has a wave-length of 1.6 $\mu$m is irradiated onto a living organism, the laser beam does not scatter within the living organism, but is locally absorbed to cause incision and vaporization of the living organism. This is due to the fact that the absorption coefficient is as high as 200 $cm^{-1}$ against the laser beam which has a wave-length of 10.6 $\mu$m while the scattering coefficient is 0 (zero).

On the other hand, when a YAG laser beam which has a wave-length of 1.06 $\mu$m is irradiated onto a living organism, the absorption coefficient of the living organism is as low as approximately 1/200 of the $CO_2$ laser beam, but the scattering coefficient becomes as high as 10 $cm^{-1}$ so that the laser beam penetrates into the living organism. Therefore, the YAG laser beam is known to be more suitable for coagulation of a living organism rather than for incision thereof.

An Ar laser beam which has a wave-length of 0.53 $\mu$m has an absorption characteristic that it can be well absorbed by hemoglobin in the blood. An identical effect is realized by the second harmonics of the YAG laser beam of 0.503 $\mu$m.

According to clinical data reported from various facilities, the $CO_2$ laser cannot independently stop bleeding if the blood vessel diameter exceeds 1 mm. On the other hand, it is reported that the YAG laser does not have sufficient ability to perform an incision on a living organism.

Therefore, in laser surgery, it is almost impossible to carry out a bloodless operation by separately and independently using the $CO_2$ surgical laser, the YAG surgical laser or the Ar surgical laser. It is desirable to irradiate a plurality of laser beams of different wave-lengths to produce a combination of different effects due to the different wave-lengths.

Conventionally, a proposal has been disclosed in Japanese Laid-Open Patent Applications No. 19136/80 and No. 81643/80, in which both the $CO_2$ laser beam and the YAG laser beam are irradiated by a single apparatus. Thus, according to the prior arts, the apparatus irradiates a plurality of laser beams of different wave-lengths so as to effectively utilize the interaction of individual laser beams for medical treatments.

The above-mentioned prior arts disclose only that a plurality of laser beams are simply blended and irradiated. Therefore, the prior arts do not provide an apparatus which can perform medical treatment in the best condition for the various living organism and they cannot fully attain desired complex medical treatment effects, because each living organism requires a different type of medical treatment according to the local condition of the living organism and, therefore, requires specific blood-stopping action and vaporization of the living organism. Furthermore, in a particular case, the best laser output is determined according to the condition of the affected part of the living organism.

The conventionally known $CO_2$ surgical laser apparatus normally consists of a $CO_2$ laser resonator, output variation means for adjusting discharge current of the $CO_2$ laser resonator, output variation signal means for controlling the output variation means, output setting means for setting oscillation outputs and a light guide for leading the laser beams from the resonator to desired positions.

Similarly, the conventionally known YAG surgical laser apparatus normally consists of a YAG laser resonator, output variation means for adjusting the exciting flash-lamp output of the YAG laser resonator, output variation signal means for controlling the output variation means, output setting means for setting ocsillation outputs and a light guide for leading the laser beams from the resonator to desired positions. Also, the conventional Ar surgical laser apparatus consists of similar components.

SUMMARY OF THE INVENTION

This invention has been made to overcome the defects of the conventional apparatus.

One of the objects of the present invention is to provide a laser irradiating apparatus with a plurality of laser beams, each having a different wave-length from each other so as to obtain complex effects of medical treatment. The arrangement of the apparatus according to the present invention is such that the mixing ratio of the laser beams and the laser output are freely varied to set a desirable irradiation condition so that medical treatments can be carried out under the best (or optimum) condition for particular living organisms.

Another object of the present invention is to provide a laser irradiating apparatus which is effective not only in the medical field but also in laser processing. In performing work on solid articles, the reflectivity of the solid material and a condensation spot size of the laser beam depend on the wave-length. Therefore, the plurality of laser beams are blended in a desirable mixing ratio and radiated to obtain a desirable complex result.

DETAILED DESCRIPTION OF THE PREFERRED EMBODIMENT

Figure 1:
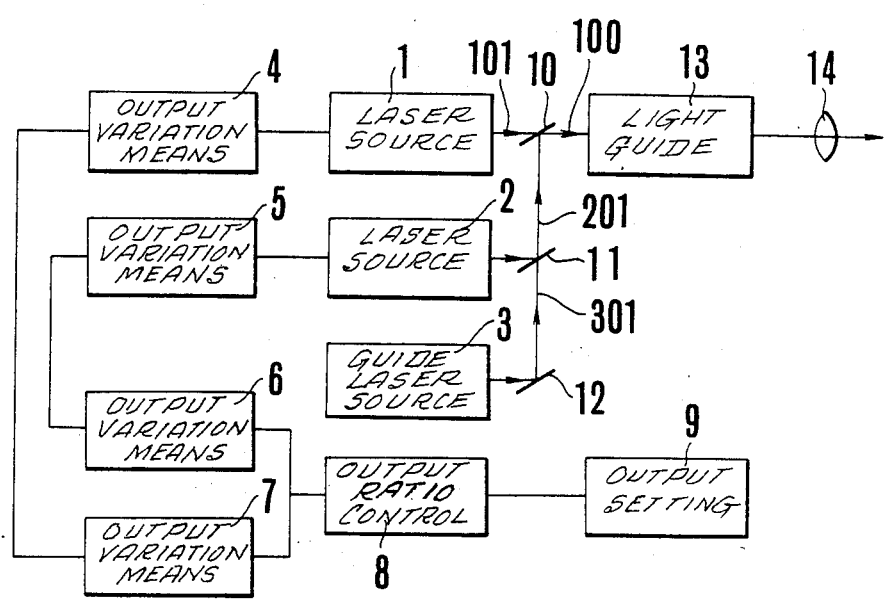
FIG. 1 is a schematic plan view showing an embodiment of the present invention.

The present invention will be described with reference to the attached drawings.

Numeral 1 indicates a first laser source. In this case, a $CO_2$ laser resonator is used. A YAG laser resonator is used as a second laser source 2. A He-Ne resonator laser is used as a guide laser source 3.

Each of laser beams 101, 201 and 301 irradiated from the sources 1, 2 and 3, respectively, is co-axially superposed one upon another in a known method using dichroic mirrors 10, 11 and a reflective mirror 12.

It goes without saying that the beam 201 irradiated from the source 2 is reflected by the dichroic mirror 11, but the beam 301 irradiated from the source 3 transmits through the mirror. The beam 101 irradiated from the source 1 transmits through the dichroic mirror 10, while both beams 201 and 301 are reflected thereby.

The superposed laser beam 100 is introduced to a light guide 13 and focused through a condensing lens 14. Then, the focused beam is irradiated on the part which is required to be irradiated. An articulated arm light guide and/or an optical fiber are used as the light guide 13.

A first laser output variation means 4 is connected to the first laser source 1. Further, a second laser output variation means 5 is connected to the second laser source 2 in an identical manner as in the case of the first laser source 1. As known, the first laser output variation means 4 is a means to adjust the discharge current of the first laser source 1. The second laser output variation means 5 is a means to adjust the excitation flash-lamp output of the second laser source 2. In other words, the output variation means 4 and 5 are the means to adjust the oscillation output of the laser sources 1 and 2, respectively.

Needless to say, these output variation means 4, 5 comprise each a high voltage circuit for introducing a high voltage to the laser beam sources 1, 2.

A first output variation signal means 7 is connected to the first laser output variation means 4. A second output variation signal means 6 is connected to the second laser output variation signal means 4. The output variation means 6 and 7 are of well-known construction, and provide signals to control the first and second laser output variation means.

In other words, the first laser output variation means 4 is operated by signals from the first output variation signal means 7, and the discharge current is controlled in such a manner that an output of the first laser source 1 is set as an optional (i.e., selectively controlled) value. In an identical manner, the second output variation means 5 is operated by the signals from the second output variation signal means 6, and the exciting flash-lamp output is controlled to set the output of the second laser source 2 as an optional (i.e., selectively controlled) value.

Needless to say, these output variation signal means 6, 7 are each a low-voltage circuit for controlling the output variation means 4, 5.

An output setting means 9 outputs signals to set the output of the laser sources 1 and 2 in the lamp. The signals are then input to a mixed ratio setting means 8. When appropriate signals are input, the mixed ratio setting means 8 outputs signals to set outputs of the first and the second laser sources 1 and 2 independently. Namely, the means 8 varies the output ratio of the first and the second sources 1 and 2. Of course, the input of the signals to the first and the second output variation signal means 6 and 7 controls the laser output.

Figure 2:
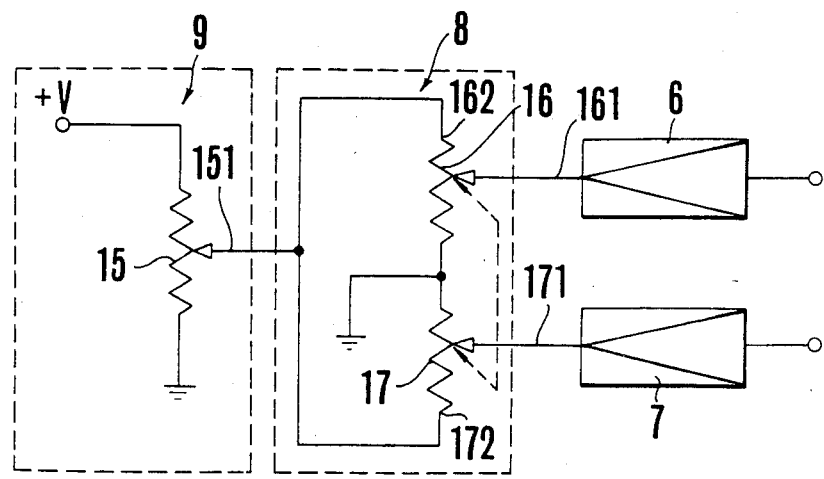
FIG. 2 is a diagram showing an example of the output setting means 9 and the mixed ratio setting means 8.

FIG. 2 shows an arrangement of the output setting means 9 and the mixed ratio setting means 8 which are illustrated in FIG. 1.

As shown in FIG. 2, the output setting means 9 applies DC voltage V to one end of a single variable resistor 15. The other end of the variable resistor 15 is earthed. The signal voltage obtained from a sliding terminal 151 of the variable resistor 15 is input to the mixed ratio setting means 8.

The mixed ratio setting means 8 consists of two variable resistors 16 and 17 and the signal voltage is input to terminals of fixed resistances 162 and 172 of the resistors 16 and 17. The other ends of the resistors 16 and 17 are earthed. The signal voltage obtained between the sliding terminal 161 of the resistor 16 and its earth, is an increased signal voltage. On the other hand, the signal voltage obtained between the sliding terminal 171 of the resistor 17 and its earth, is a decreased signal voltage. Therefore, when the decreased signal terminal has a maximum value, the increased signal terminal has a 0 (zero) value. However, when the increased signal terminal has a maximum value, the decreased signal terminal has a 0 (zero) value. The arrangement is such that signal voltages obtained from sliding resistance terminals 161 and 171 are converted to signals which regulate the output ratio of the first and the second laser sources 1 and 2.

As mentioned above, the signals which are output from the mixed ratio setting means 8 are input to the first and the second output variation signal means 6 and 7 to determine the output of the laser sources 1 and 2. Therefore, the output ratio of the laser sources 1 and 2 is optionally (i.e., selectively) controlled by adjusting the mixed ratio setting means 8. Also, the output of the laser sources 1 and 2 is optionally controlled by adjusting the output setting means 9.

Figure 3:
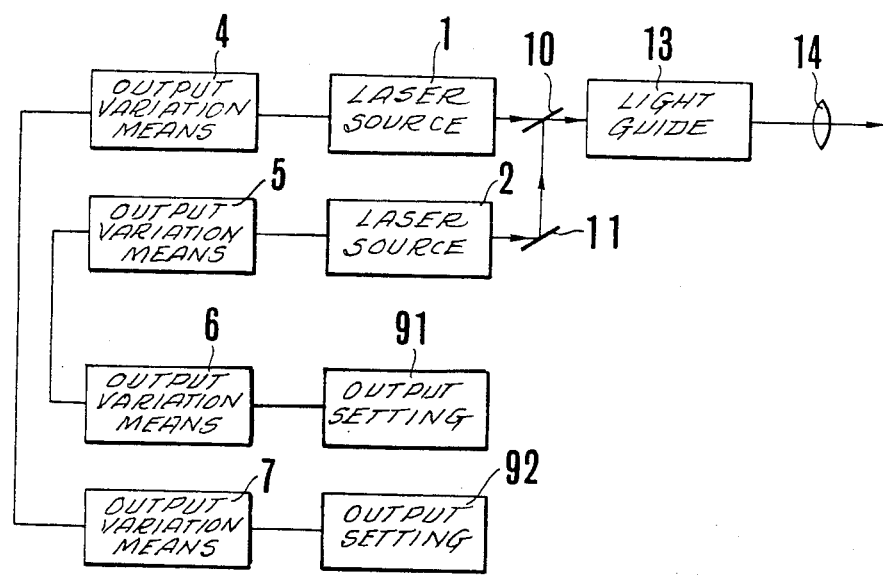
FIG. 3 is a schematic plan view showing another embodiment of the present invention.

The second embodiment of the present invention is described below referring to FIG. 3. In FIG. 3, the same numerical references as in the first embodiment signify the identical part of the second embodiment. In this embodiment, however, the guide laser source is omitted.

In the second embodiment, the control of the output of the first laser source 1 and the second laser source 2 is separately and independently carried out. For example, the output signal from the first output setting means 92 is input to the first output variation signal means 7, which outputs a signal to control the first laser output variation means 4. Of course, the signal is input to the first laser output variation means 4 and the means 4 controls the output of the first laser source 1. As in the case of the first embodiment, $CO_2$ laser is used as the first laser source 1. The output power of the laser source 1 is adjusted by controlling the discharge current.

The output of the second laser source 2 is controlled by the second output setting means 91, the second output variation signal means 6, and the second laser output variation means 5. The YAG laser is used as the second laser source 2 and the output is adjusted by controlling the output of the exciting flash-lamp.

Needless to say, these output setting means 91, 92 have a similar structure as the output setting means 9 in the first embodiment described hereinbefore.

Laser beams from the first and the second laser sources 1 and 2 are co-axially superposed on each other and irradiated through a light guide 13. In the second embodiment, the output of the first laser source 1 and the second laser source 2 are separately and independently controlled by adjusting the first output setting means 92 and the second output setting means 91 independently. Therefore, the output ratio of the first laser source 1 and the second laser source 2 are desirably set by adjusting the means 91 and the means 92 suitably.

Figure 4:
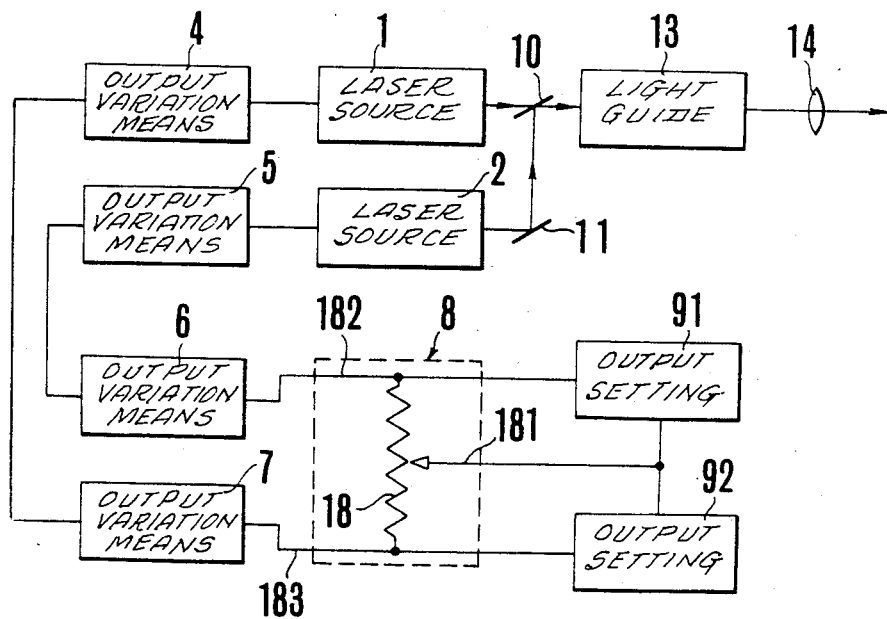
FIG. 4 is a schematic plan view showing further another embodiment of the present invention.

FIG. 4 shows still another arrangement for a third embodiment. In this case, the guide laser source is omitted. The same numerals as used in the first and the second embodiments signify the identical components.

As shown in the drawing, output setting means 92, 91 are provided, corresponding to the first laser source 1, and the second laser source 2, respectively. The signals from the output setting means are input to the mixed ratio setting means 8.

The mixed ratio setting means 8 consists of a variable resistor 18 and varies the signal voltages which are output from the fixed resistance terminals 182 and 183 by operating the sliding resistance terminal 181. The signal output from the fixed resistance terminal 182 is input to the second output variation signal means 6. And, the output of the second laser source 2 is determined by operating the second laser output variation means 5. The signal output from the fixed resistance terminal 183 inputs to the first output variation signal means 7. And, the output of the first laser source 1 is determined by operating the first laser output variation means 4.

Therefore, in the third embodiment, the output ratio of the sources 1 and 2 is controlled by adjusting the mixed ratio setting means 8. Also, the output ratio is controlled by adjusting the output setting means 91 and 92 because the adjustment of means 91 and 92 results in independent changes of the output of the sources 1 and 2.

It is understood from the above description that the present invention provides a laser irradiating apparatus which irradiates a plurality of laser beams having different wave-lengths. The apparatus includes means to vary the output of each laser source, and means to optionally vary the output ratio. Therefore, when used in the field of medical treatment, the apparatus can select the output and the most suitable output ratio of the laser beams in response to the condition. Consequently, the medical treatment to a living organism can be performed under the most suitable condition.

Therefore, desired complex medical treatment effects can be fully achieved.

In the second embodiment, no mixing ratio setting means is provided, but the ratio of the laser output can be easily varied by adjusting the output setting means corresponding to the respective laser beam sources. Thus, the second embodiment shown above is within the scope of the present invention.

The apparatus according to the present invention can effectively be used for laser processing on various articles. As mentioned above, working on articles requires variation of wave-length. For example, reflectivity of the material varies depending on the wave-length of the irradiated laser beam. Further, when the wave-length of the laser beam is made shorter, the condensation spot size of the beam becomes smaller and the power density is increased. According to the present invention, various types of work such as drilling, cutting, hardening, and welding can be carried out on various kinds of material. Further, simultaneous irradiation of the plurality of laser beams each having a different wave-length from each other, enables complex effects which cannot be expected from the irradiation of a single laser beam.

It is to be understood that the present invention is not limited to the embodiments described above, but, as defined in the appended claims, many apparently widely different embodiments of the present invention may be made without departing from the spirit and scope thereof. For example, the output setting means 9, the mixed ratio setting means 8 may comprise a digital circuit, or a microcomputer.

Further, the first laser source 1 and the second laser source 2 are not limited to the $CO_2$ laser and the YAG laser. For example, an Ar laser and a CO laser may be used in place of them. The number of laser sources will not be limited to two (2). It is the gist of the present invention to provide the laser irradiating apparatus which uses a plurality of laser resonators to irradiate the laser beams each of which has a different wave-length from others for obtaining the interaction between the laser beams and the materials to be irradiated.

Still further, the laser beams irradiated from the plurality of laser sources are not limited to CW oscillation. In some cases, the CW oscillation and the pulse oscillation can be used together. In some other cases, only the pulse oscillation can be used. In this particular case, it is possible to make the pulse oscillation of the YAG laser to a Q-switched pulse and that of the $CO_2$ laser to a high peak pulse by use of a gain-switch, etc.

What we claim:

1. A laser irradiating apparatus adapted for simultaneously or selectively irradiating laser beams on an object, comprising:

a plurality of laser sources each outputting laser beams of different wave-length;

optical means for co-axially overlapping the laser beams;

light guide means for transmitting the overlapped laser beams respectively to a desired portion of the object to be irradiated;

a plurality of laser output variation means, connected individually and respectively to each of the laser sources, for introducing a high voltage to each of the laser sources;

a plurality of laser output variation signal means, responsive to input signals, for controlling respective of the laser output variation means;

mixing ratio setting means for providing input signals to the laser output variation signal means to vary the output ratio of the plurality of laser sources; and laser output setting means, connected to the mixing ratio setting means, for controlling said mixing ratio setting means to thereby set the outputs of the laser sources.

2. A laser irradiating apparatus according to claim 1, in which the plurality of laser sources comprises:

a first laser source for outputting a first laser beam adapted to be effective primarily for incision of said object, and a second laser source for outputting a second laser beam adapted to be effective primarily for solidification of said object, wherein the mixing ratio setting means divides the signal output from one output setting means into two signals in a desired ratio and outputs said two signals respectively to ones of said laser output variation signal means.

3. A laser irradiating apparatus according to claim 1, the plurality of laser sources comprising:

a first laser source for outputting a first laser beam adapted to be effective mainly for incision of said object, a second laser source for outputting a second laser beam adapted to be effective mainly for solidification of said object, the output setting means comprising a first output setting means corresponding to the first laser source and a second output setting means corresponding to the second laser source, wherein the mixing ratio setting means receives signals from each of the first and second output setting means and converts them in a desired ratio to output them respectively to one of the laser output variation signal means.

* * * * *